(12) United States Patent
Zhu et al.

(10) Patent No.: US 11,986,380 B2
(45) Date of Patent: May 21, 2024

(54) BENDING-RESISTANT NERVE CATHETER AND PREPARATION METHOD AND APPLICATION THEREOF

(71) Applicants: Neosheng (Tianjin) Biotechnology Co., Ltd, Tianjin (CN); Nankai University, Tianjin (CN)

(72) Inventors: Meifeng Zhu, Tianjin (CN); Deling Kong, Tianjin (CN); Xianhao Dong, Tianjin (CN); Guangzhou Song, Tianjin (CN)

(73) Assignees: Neosheng (Tianjin) Biotechnology Co., Ltd, Tainjin (CN); Nankai University, Tainjin (CN)

( * ) Notice: Subject to any disclaimer, the term of this patent is extended or adjusted under 35 U.S.C. 154(b) by 0 days.

(21) Appl. No.: 18/310,306

(22) Filed: May 1, 2023

(65) Prior Publication Data

US 2023/0363881 A1 Nov. 16, 2023

(30) Foreign Application Priority Data

May 11, 2022 (CN) .......................... 202210510177.0

(51) Int. Cl.
*A61F 2/02* (2006.01)
*A61F 2/00* (2006.01)
(Continued)

(52) U.S. Cl.
CPC .............. *A61F 2/0077* (2013.01); *A61F 2/04* (2013.01); *D01D 5/0007* (2013.01); *D01D 5/06* (2013.01);
(Continued)

(58) Field of Classification Search
CPC .. A61F 2/0077; A61F 2/04; A61F 2002/0086; D01D 5/06; D01D 5/08;
(Continued)

(56) References Cited

U.S. PATENT DOCUMENTS

2012/0150205 A1* 6/2012 Park .......................... D01F 4/02
606/152
2018/0304553 A1 10/2018 Park

FOREIGN PATENT DOCUMENTS

| CN | 101912318 A | 12/2010 |
| CN | 106075596 A | 11/2016 |

(Continued)

OTHER PUBLICATIONS

Fregnan, et al. "Preclinical Validation of SilkBridge for Peripheral Nerve Regeneration" Frontiers in Bioenengineer and Biotechnology, Aug. 7, 2020.

*Primary Examiner* — Dinah Baria
(74) *Attorney, Agent, or Firm* — Stuart H. Mayer; Kaplan Breyer Schwarz LLP

(57) ABSTRACT

Disclosed is a bending-resistant nerve catheter and a preparation method and application thereof, and relates to the technical field of tissue engineering materials. The catheter of the present application includes an inner layer, a middle layer and an outer layer, and each layer uses raw materials of biodegradable polymers; among them, the inner layer includes a smooth surface inner layer, an oriented microchannel inner layer or a fibrous inner layer, the middle layer is a fibrous middle layer with crossing angles, the middle layer is prepared by entangling micron fibers with a certain angular arrangement, and the outer layer is made of randomly entangled polymer fibers and is tightly bonded to the middle layer.

5 Claims, 15 Drawing Sheets

(51) Int. Cl.
  *A61F 2/04* (2013.01)
  *D01D 5/00* (2006.01)
  *D01D 5/06* (2006.01)
  *D01D 5/08* (2006.01)

(52) U.S. Cl.
  CPC ........ *D01D 5/08* (2013.01); *A61F 2002/0086* (2013.01); *D10B 2201/00* (2013.01); *D10B 2331/10* (2013.01); *D10B 2401/062* (2013.01); *D10B 2401/12* (2013.01); *D10B 2509/00* (2013.01)

(58) Field of Classification Search
  CPC .............. D01D 5/0007; A61L 2430/32; D10B 2201/00; D10B 2331/10; D10B 2401/12
  See application file for complete search history.

(56) References Cited

FOREIGN PATENT DOCUMENTS

| | | |
|---|---|---|
| CN | 111035811 A | 4/2020 |
| CN | 111068118 A | 4/2020 |
| CN | 113365673 A | 9/2021 |

* cited by examiner

BENDING-RESISTANT NERVE CATHETER AND PREPARATION METHOD AND APPLICATION THEREOF

CROSS-REFERENCE TO RELATED APPLICATIONS

This application claims priority to Chinese Patent Application No. 202210510177.0, filed on May 11, 2022, the contents of which are hereby incorporated by reference.

TECHNICAL FIELD

The present application relates to the technical field of tissue engineering materials, and in particular to a bending-resistant nerve catheter and a preparation method and application thereof.

BACKGROUND

Peripheral nerve damage occurs for a variety of reasons, including trauma, disease or surgery, resulting in loss of sensory and motor function or even permanent muscle movement disorders. There are approximately 96 million people worldwide with peripheral nerve injuries, and the number of patients who experience functional impairment after a peripheral nerve injury is nearly 20 million in China, which is increasing at a rate of 2 million per year, causing a serious burden to patients, families and society. Currently, an end-to-end suture is employed in preference for small size (<5 millimeters) nerve defects in clinical practice. whereas for nerve defects of longer distances, an autonomous graft or allograft is often performed. However, autografts require secondary surgery and cause secondary damage to the body, leading to impaired nerve function or traumatic neuroma formation in the donor area, with the problem of mismatch in the size of the nerves taken as well. In contrast, allografts have restricted clinical applications as a result of limited supplies. In this regard, the nerve catheter is developed in the tissue engineering field to provide a new approach to peripheral nerve repair, replacing autologous and allogeneic grafts to bridge the nerve injury site and providing a bionic microenvironment for axonal regeneration.

More than a dozen nerve catheter products have been developed for clinical repair of nerve defects and have been reported to be effective in promoting nerve recovery. However, feedback from clinicians and reports suggest that some natural materials, such as collagen nerve catheters, are not mechanically strong enough to be implanted in a muscular environment and are subject to reduction in lumen volume upon muscle compression, thereby inhibiting nerve growth. Also, most products used to repair nerve defects in human joints are not bending resistant and will cause compression and distortion of the internal volume of the catheter during joint flexion, thus hampering nerve growth. Flexion of the joint may also cause the sutures to be withdrawn which may induce secondary nerve damage, while the problems of post-operative stiffness, tissue adhesions and muscle atrophy are more likely to occur if the joint is immobilized for a prolonged period of time during the nerve repair process. Therefore, an ideal nerve catheter is one that is biocompatible and provides a suitable microenvironment for nerve growth, whilst being resistant to muscle compression, flexible and resistant to bending, and such an ideal nerve catheter is urgently needed to solve the problem of nerve deficits in the muscle environment and across joints.

SUMMARY

In order to address the above-mentioned problems of the prior art, the present application provides a bending-resistant nerve catheter and its preparation method and application, the provided catheter has superior bending resistance and nerve repair performance.

In order to achieve the above objectives, the present application provides the following technical schemes:
one of the objectives of the present application is to provide a bending-resistant nerve catheter, including an inner layer, a middle layer and an outer layer, where the inner layer, the middle layer and the outer layer are made of raw materials of biodegradable polymers;
the inner layer is a smooth surface inner layer, an oriented microchannel inner layer, or a fibrous inner layer;
the middle layer is a fibrous middle layer of crossing angles, and the crossing angles are in a range of 0-90 degrees (°), excluding 0°; and
the outer layer is a fibrous outer layer distributed randomly.

Optionally, the bending-resistant nerve catheter has a lumen diameter of 1-100 millimeters (mm) and a wall thickness of 50-1,000 micrometers (um).

Optionally, the smooth surface inner layer has a thickness of 1-100 um; the oriented microchannel inner layer is prepared by a method of reverse template with a thickness of 1-200 um, and the oriented microchannel has a groove depth of 1-100 um; and the fibrous inner layer is prepared by magnetic field-assisted electrostatic spinning, with a fiber diameter of 0.1-200 um and a thickness of 0.1-200 um.

Optionally, the fibrous middle layer of crossing angles is prepared by a method of wet spinning or melt spinning.

Optionally, the method of wet spinning prepares fibers with a diameter of 5-300 um, thereby developing a middle layer with a thickness of 20-450 um; and the method of melt spinning prepares fibers with a diameter of 1-100 um, thereby developing a middle layer with a thickness of 20-500 um.

Optionally, the fibrous outer layer includes fibers of a diameter of 0.01-200 um, and the outer layer has a thickness of 10-400 um.

Optionally, the biodegradable polymers include one or more of synthetic degradable polymers or natural polymer materials.

Optionally, the synthetic degradable polymers include polylactic acid (PLA), polycaprolactone (PCL), poly(L-lactide-caprolactone) (PLCL), polyhydroxyalkanoates (PHA), poly(lactic-co-glycolic acid) (PLGA), polydioxanone (PDS) or polyurethane (PU); and the natural polymer materials include collagen, gelatin, silk fibroin, fibrin, chitosan, chitin, cellulose, starch, alginic acid or hyaluronic acid.

Another objective of the present application is to provide a preparation method of the bending-resistant nerve catheter, including preparing the inner layer by a template method or a magnetic field-assisted electrostatic spinning method, then preparing the middle layer by a wet spinning method or a melt spinning method, and preparing the outer layer by an electrostatic spinning method.

Another objective of the present application is to provide an application of the bending-resistant nerve catheter in preparing nerve repair materials.

Specifically, the bending-resistant nerve catheter is used for repairing nerves, blood vessels, lymphatic vessels, urethra, lacrimal ducts or intestinal tissues.

In recent years, some similar research has been conducted on the design and development of catheters to meet the actual clinical need for nerve catheters resistant to compression and bending, yet the number is limited. Of the products available for clinical use, only Stryker's Neuroflex™ is bend-resistant, with a bending angle of 60°. In view of solving the problems of poor compression and bending resistance of the existing products and the short distance and poor effectiveness of nerve repair, the present application designs and prepares a catheter of triple-layer structure composed of an inner layer, a middle layer and an outer layer with a smooth inner structure or with a channel structure and bending resistance.

The inner layer of the catheter provided by the present application includes a smooth surface, an oriented microchannel or a dense thin layer of fibers, which accelerates nerve growth and prolongs its repair distance with the help of smooth structure or oriented guidance structure of the inner layer; moreover, the dense inner layer is also capable of providing axial mechanical support; the middle layer is formed by the entanglement of micron fibers arranged at certain angles, with the main function of making the catheter flexible and resistant to bending, while providing radial mechanical support; and the outer layer is formed by polymer fibers entangled randomly and bonded tightly to the middle layer, mainly to prevent surrounding tissue cells from infiltrating into the catheter and impeding nerve growth; the catheter has a lumen diameter of 1-100 mm and a wall thickness of 50-1,000 um.

The present application achieves the following technical effects:

the present application is a triple-layered catheter consisting of an inner layer, a middle layer and an outer layer, where the inner layer of the catheter is a smooth surface inner layer, or an oriented microchannel inner layer or directional fibrous inner layer, capable of guiding the directional migration of cells; the middle layer of the catheter is a fibrous structure with crossing angles (0-90°), endowing the catheter with flexibility, resistance to folding and muscle compression, and therefore preventing the catheter from blockage due to folding; and the outer layer of random distributed fibers prevents the migration of surrounding cells; and the preparation method of the catheter of the present application is highly controllable, allowing the thickness, smoothness, microchannel and fiber diameter of the inner layer, the diameter of the middle layer and the angles and degree of bonding between the fibers, and the size and thickness of the outer layer to be adjusted; the diameter and thickness of the catheter is also controlled; the catheter of the present application is used for the repair of nerves, blood vessels, lymphatic vessels, urethra, tear ducts and intestinal tissues.

BRIEF DESCRIPTION OF THE DRAWINGS

To illustrate more clearly the technical schemes in the embodiments of the present application or in the prior art, a brief description of the accompanying drawings to be used in the embodiments are given below. It is obvious that the accompanying drawings in the following description are only some embodiments of the present application and that other accompanying drawings are available to those of ordinary skill in the art without any creative effort.

DETAILED DESCRIPTION OF THE EMBODIMENTS

A number of exemplary embodiments of the present application are now described in detail, and this detailed description should not be considered as a limitation of the present application, but should be understood as a rather detailed description of certain aspects, characteristics and embodiments of the present application.

It is to be understood that the terms described in the present application are intended to describe particular embodiments only and are not intended to limit the present application. Further, with respect to the range of values in the present application, it is to be understood that each intermediate value between the upper and lower limits of the range is also specifically disclosed. Each smaller range between any stated value or intermediate value within a stated range and any other stated value or intermediate value within a stated range is also included in the present application. The upper and lower limits of these smaller ranges may be independently included or excluded from the scope.

Unless otherwise stated, all technical and scientific terms used herein have the same meaning as commonly understood by those of ordinary skill in the field described in the present application. Although the present application describes only preferred methods and materials, any methods and materials similar or equivalent to those described herein may also be used in the implementation or testing of the present application. All literature referred to in this specification is incorporated by reference for the purpose of disclosing and describing the methods and/or materials associated with the literature described. In the event of conflict with any incorporated literature, the contents of this specification shall prevail.

Various improvements and variations may be made to specific embodiments of the specification of the present application without departing from the scope or spirit of the present application, as will be apparent to those skilled in the art. Other embodiments obtained from the specification of the present application are obvious to those skilled in the art. The specification and embodiments of the present application are exemplary only.

The terms "including", "comprising", "having" and "containing" used in this specification are all open terms, which means including but not limited to.

Figure 5:
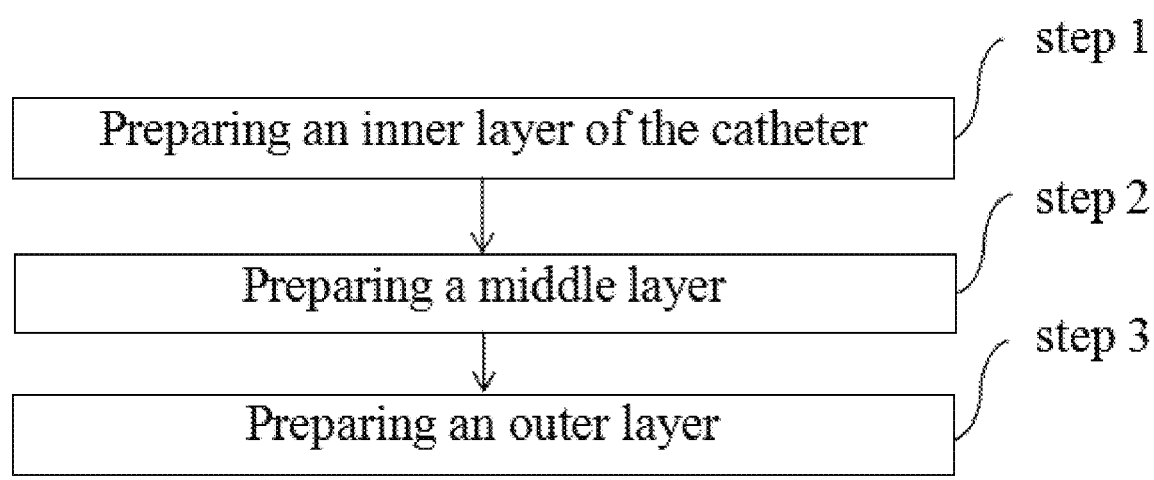
FIG. 5 illustrates a process of a preparation method of the bending-resistant nerve catheter provided by the present application.

The present application provides a triple-layered bending-resistant nerve catheter prepared by a method of three steps as shown in FIG. 5, including:

step 1, preparing an inner layer of the catheter, including preparing an oriented microchannel inner layer by a method of reverse template (or preparing a smooth inner layer by receiving using a smooth metal receiving rod, or preparing a fibrous inner layer by magnetic field-assisted electrostatic spinning;

the oriented microchannel inner layer is prepared by a method illustrated as follows: the chemically pure reagent (including acetic acid, water, tetrahydrofuran, dichloromethane, chloroform, acetic acid, acetone, trifluoroethanol, hexafluoroisopropanol, etc.) are used as solvents to prepare a solution of degradable polymers at a certain concentration (1-60% by mass/volume), including polycaprolactone (PCL), polylactic acid (PLA), poly(lactic-co-glycolic acid) (PLGA), polyglycolic acid (PGA), polyhydroxyalkanoates (PHA), and poly(L-lactide-caprolactone) (PLCL), polydioxanone (PDS), etc., or of natural materials, including silk fibroin, chitosan, gelatin, collagen, etc.; and the solution dissolved with polymer material is filled into a syringe after complete dissolving; then the polymer solution in the syringe is printed onto a receiving rod with oriented microchannel below the needle by using a micro-injection pump, where the receiving rod has a diameter of 1-100 mm, the microchannel has a width of 0.1-50 um and a depth of 0.1-50 um; the flowing rate of the solution is 0.1-50 millimeters per liter (mL/h), and the syringe needle is distanced from the oriented microchannel for 0.1-5 centimeters (cm); the receiving rod rotates in a speed of 1-500 revolutions per minute (rpm) and moves in a speed of 1-50 millimeters per second (mm/s); the solvent in the extruded polymer solution volatilizes, and a thin film with oriented microchannel in the inner layer is formed after curing; the thickness of the oriented microchannel inner layer can be controlled in a range of 1-200 um by adjusting parameters such as polymer concentration, flowing rate, diameter, and rotating speed and moving speed of the receiving rod;

the fibrous inner layer is prepared by a preparation method as follows: chemically pure reagents (including acetic acid, formic acid, water, tetrahydrofuran, dichloromethane, chloroform, acetic acid, acetone, trifluoroethanol, hexafluoroisopropanol, etc.) are used as solvents to prepare degradable polymers with a certain concentration (mass/volume fraction of 1%-60%), including PCL, PLA, PLGA, PGA, PHA, PLCL, PDS, or natural material solutions of silk fibroin, chitosan, gelatin, collagen, etc.; after complete dissolution, the dissolved synthetic or natural material solution is filled into a syringe, the receiving rod is installed on a magnetic field-assisted electrostatic spinning apparatus, then the syringe filled with the polymer solution is installed on an injection pump, with a needle of the syringe placed at a position 1-20 cm above the receiving rod; the conditions are set as follows: a voltage of 0.1-100 kilovolts (KV), a speed of the injection pump of 0.1-40 milliliters per hour (mL/h), a rotating speed of the receiving rod of 1-1,000 rpm, a moving speed of the receiving rod of 1-1,000 millimeters per second (mm/sec), and a spinning duration of 1-100 min; then the spinning is carried out to obtain fibers for later use; an inner layer with a controlled and axially oriented fiber diameter (0.1-200 um) and a thickness of 0.1-200 um is prepared by adjusting parameters such as concentrations of polymers or natural materials, flowing rate, rotating speed and moving speed of the receiving rod;

step 2, preparing a middle layer of microfibers with crossing angles of the catheter; specifically, the middle layer is prepared by the method of wet spinning or melt spinning, where the receiving rod with the oriented microchannel inner layer, oriented fibers or smooth surface prepared after the step 1 is mounted on the wet spinning apparatus, the syringe is filled with the polymer solution or natural material solution of certain concentration, and the syringe is mounted on the injection pump, and the parameters such as syringe advancing speed, rotating speed and moving speed of the receiving rod are adjusted to regulate the diameter of the micron fibers in the middle layer and also the angles between the fibers, so as to prepare circumferentially oriented fibers with a diameter of 5-300 um and a thickness of 20-450 um; in addition, it is also feasible to mount the receiving rod with inner layer of oriented microchannel or oriented fibers or smooth surface prepared in the step 1 on the melting spinner, and add the polymers to the thermostatically heated barrel, which is heated to melt the polymers, then the parameters such as advancing speed of the barrel piston, needle diameter, rotating speed and lateral moving speed of the receiving rod are adjusted to regulate the diameter of the micron fibers in the middle layer and the crossing angles between the fibers to produce a middle layer of intertwined fibers with a diameter of 1-100 um and a thickness of 20-500 um; and step 3, preparing an outer layer of randomly distributed fibers of the catheter; the randomly distributed fibers of the outer layer is prepared by a preparation method as follows: the chemically pure reagents (including tetrahydrofuran, dichloromethane, chloroform, acetic acid, acetone, trifluoroethanol, hexafluoroisopropanol, etc.) are used as solvents to prepare degradable polymer solutions with a certain concentration (mass/volume fraction of 1%-60%), including PLCL, PLA, PLGA, PGA, PHA, PLCL, PDS, or natural material solutions of silk fibroin, chitosan, gelatin, collagen, etc.; after complete dissolution, the dissolved synthetic or natural material solution is loaded into a syringe mounted on an injection pump, and the receiving rod containing the inner and middle layers of the catheter prepared in the step 2 is placed on an electrostatic spinning apparatus, and the syringe needle is placed at a position 1-40 cm above the receiving rod, where the voltage is set to 0.1-100 KV, the advancing speed of the injection pump is 0.1-40 mL/h, the rotating speed of the receiving rod is 1-1,000 rpm, and the moving speed of the receiving rod is 1-1,000 mm/sec, the spinning duration is 1-100 min; then the organic solvent is vacuumed off after the process is completed; and the outer layer of randomly distributed fibers with a controlled diameter of 0.01-200 um and thickness of 10-400 um is produced by adjusting parameters such as polymer concentrations, flowing rate, and rotating speed and moving speed of the receiving rod.

Embodiment 1 Preparation of Triple-Layered PCL Catheter

The PCL used in this embodiment has an average molecular weight of 60,000, and the PCL solutions used are all PCL chloroform solutions (PCL content expressed as mass/volume concentration).

The preparation follows a process as follows:
(1) preparation of the inner layer of the catheter: 2.0 grams (g) PCL is weighed and added into 10 mL chloroform, and stirred and dissolved overnight at room temperature to prepare a PCL solution with a concentration fraction of 20% (mass/volume); then the inner layer of the catheter is prepared by uniformly printing the solution as ink printing in a fume hood under room temperature; specifically, a stainless steel receiving rod with microchannel and a diameter of 2.0 mm is installed on a printer, then the PCL solution is sucked into a syringe, which is then installed on the injection pump, with syringe needle placed 1 mm above the stainless steel receiving rod; the advancing speed of the injection pump is 2 mL/h, the rotating speed of the receiving rod is set at 100 rpm, the lateral moving speed is 0.2 mm/sec, and the printing is carried out for a duration of 10 min; after preparation, the receiving rod with an inner layer of 50 um thickness and a microchannel groove depth of 20 um is vacuum dried;
(2) preparation of the middle layer of the catheter: the catheter is prepared by wet spinning in a fume hood under room temperature, specifically, the receiving rod with the inner layer is installed on a wet spinning apparatus, 15% PCL spinning solution is sucked into a syringe, then the syringe is installed on an injection pump, with syringe needle placed at a position 2 cm away from the receiving rod in a spinning coagulation bath, where the advancing speed of the injection pump is 2 mL/h, the rotating speed of the receiving rod is 500 rpm, the moving speed is 1 mm/sec, and the spinning duration is 30 min; after completion, the coagulation bath and the spinning solution solvent are removed, and the finished middle layer has a fiber diameter of 89 um and a thickness of 400 um (with a fiber crossing angle of 15°);
(3) preparation of the outer layer of the catheter: the outer layer of the catheter is prepared by an electrostatic spinning method; specifically, the receiving rod with the inner layer and the middle layer prepared after the previous two steps is installed on an electrostatic spinning apparatus, 10% PCL solution is sucked into a syringe, then the syringe is installed on an injection pump, with the needle of the syringe placed at a position 20 cm above the receiving rod, and electrostatic spinning is carried out under conditions of a voltage of 13 KV, an advancing speed of the injection pump of 1 mL/h, a rotating speed of the receiving rod of 500 rpm, a moving speed of 0.5 mm/sec, and a spinning duration of 10 min; after completion, the organic solvent is removed by vacuum; the outer layer is produced with a fiber diameter of 100 um and a thickness of 30 um; then the triple-layered catheter (total thickness of 480 um, inner diameter of 2.0 mm) is removed for characterization and for later use after completion of the outer layer spinning.

Embodiment 2 Preparation of Triple-Layered PLCL Catheter

The PLCL used in this embodiment has an average molecular weight of 100,000, and the PLCL solutions used are all PLCL acetic acid solutions (PLCL content expressed as mass/volume concentration).
(1) preparation of the inner layer of the catheter: 1.0 g PLCL is weighed and added into 10 mL of acetic acid, and stirred and dissolved overnight at room temperature to prepare a PLCL solution with a concentration fraction of 10% (mass/volume), then the inner layer of the catheter is prepared by magnetic field-assisted electrostatic spinning apparatus in a room temperature fume hood; specifically, a polytetrafluoroethylene (PTFE) receiving rod with a diameter of 3.0 mm is installed on a spinning machine, then the PLCL solution is sucked into a syringe, and the syringe is installed on a syringe pump, with the syringe needle placed at a position 20 mm above the PTFE receiving rod, the magnetic field intensity in the preparation process is 0.1 tesla (T), and the parameters are set as follows: advancing speed of the injection pump of 3 mL/h, the rotating speed of the receiving rod of 20 rpm, the moving speed of 1 mm/sec, and the spinning duration of 12 min; after preparation, the receiving rod with a 40 um thick inner layer (5 um fiber diameter) is vacuum dried;
(2) preparation of the middle layer of the catheter: the middle layer of the catheter is prepared by melt spinning in a room temperature fume hood; specifically, the receiving rod with inner layer is installed on the melt spinning apparatus, 10.0 g PLCL is added into a constant-temperature heating cylinder, which is heated to 150° C. to melt the PLCL; the speed of the piston advancing of the cylinder is set at 0.5 mL/h, the receiving rod is set with a rotating speed of 100 rpm, a moving speed of 0.5 mm/sec, and the duration is 30 min; then the middle layer with a fiber diameter of 100 um and a thickness of 450 um (fiber crossing angle of 20°) is produced;
(3) preparation of the outer layer of the catheter: the outer layer of the catheter is prepared by an electrostatic spinning method; specifically, the receiving rod with inner layer and middle layer prepared after the previous two steps is installed on an electrostatic spinning apparatus, 12% PLCL solution is sucked into a syringe, and the syringe is installed on an injection pump, with the needle of the syringe placed 30 cm above the receiving rod for electrostatic spinning, where the voltage is 20 KV, the speed of the injection pump is 3 mL/h, the rotating speed of the receiving rod is 800 rpm, the moving speed is 5 mm/sec, and the spinning duration is 13 min; after completion, the organic solvent is vacuumed off; the prepared outer layer has a fiber diameter of 1 um and a thickness of 50 um; the triple-layered catheter (total thickness 540 um, inner diameter 3.0 mm) is removed and set aside after completion of the spinning of the outer layer.

Embodiment 3 Preparation of Triple-Layered PLGA Catheter

The PLGA used in this embodiment has an average molecular weight of 40,000, and the PLGA solutions used are all PLGA acetone solutions (PLGA content expressed as mass/volume concentration).
  (1) Preparation of the inner layer of the catheter: 1.2 g PLGA is weighed and added into 10 mL of acetone, which is stirred and dissolved overnight at room temperature to prepare a PLGA solution with a concentration of 12% (mass/volume); the inner layer of the catheter is prepared by uniformly printing the solution as ink in a room temperature fume hood, including: installing a smooth stainless steel receiving rod with a diameter of 5.0 mm on the printer, sucking the PLGA solution into the syringe, installing the syringe on the syringe pump, and placing the syringe needle at a position 5 mm above the stainless steel receiving rod, setting the advancing speed of the injection pump to 1.5 mL/h, the rotating speed of the receiving rod to 500 rpm, the lateral moving speed to 5 mm/sec, and the printing duration to 30 min, and completing the preparation; after preparation, the receiving rod with a 60 um thick inner layer is vacuum dried;
  (2) preparation of the middle layer of the catheter: the middle layer of the catheter is prepared by melt spinning in a room temperature fume hood; specifically, the receiving rod with the inner layer is installed on the melt spinning apparatus, 30.0 g PLGA is added into the constant-temperature heating cylinder, which is heated to 130° C. to melt PLGA, where the speed of the piston advancing of the cylinder is set at 2 mL/h, the receiving rod is set with a rotating speed of 500 rpm, a moving speed of 1 mm/sec, and the duration is 25 min; the produced middle layer has a fiber diameter of 43 um and a thickness of 500 um (fiber crossing angle of 35°);
  (3) preparation of the outer layer of the catheter: the outer layer of the catheter is prepared by an electrostatic spinning method; specifically, the receiving rod with inner layer and middle layer prepared after the previous two steps is installed on an electrostatic spinning apparatus, 12% PLGA solution is sucked into a syringe, the syringe is then installed on an injection pump, with the needle of the syringe placed 13 cm above the receiving rod, then the electrostatic spinning is performed, where the voltage is set at 12 KV, the injection pump speed is 1.2 mL/h, the receiving rod is set with a rotating speed of 300 rpm, a moving speed of 10 mm/sec, and the spinning duration is 6 min; after completion, the organic solvent is vacuumed off, and the prepared outer layer has a fiber diameter of 0.5 um and a thickness of 30 um, then the triple-layered catheter (total thickness of 590 um, inner diameter of 5.0 mm) is removed and set aside after completion of the spinning of the outer layer.

A single-layered electrostatic spinning catheter with a fiber diameter of 5 um and a thickness of 480 um, prepared by electrostatic spinning alone (using a 10% mass volume concentration of PCL chloroform solution as the spinning solution), is used as a control to verify the relevant performance of the triple-layered catheters prepared in Embodiments 1-3.

Figure 1A:
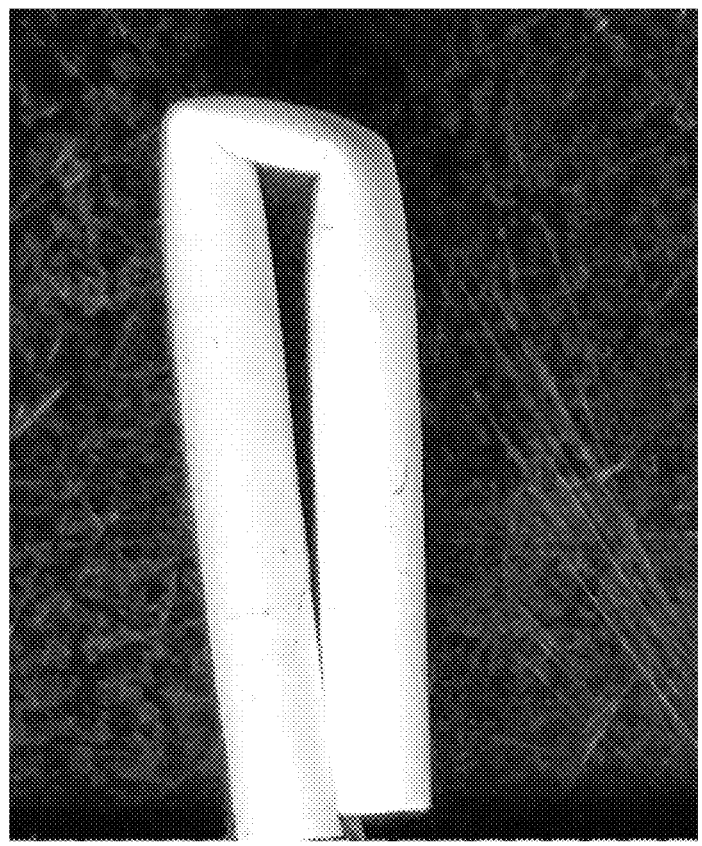
FIG. 1A shows a control electrostatic spinning catheter in terms of bending resistance.
Figure 1B:
FIG. 1B shows the bending resistance of triple-layered catheters prepared in Embodiment 1.
Figure 1C:
FIG. 1C show the bending resistance of triple-layered catheters prepared in Embodiment 2.
Figure 1D:
FIG. 1D shows the bending resistance of triple-layered catheters prepared in Embodiment 3.

The bending resistance of the triple-layered catheters prepared in Embodiments 1-3 is verified and the results are shown in FIG. 1A to FIG. 1D. As can be seen from the FIG. 1A-FIG. 1D, the control electrostatic spinning catheter is completely folded and blocked after bending of 180°, while the triple-layered catheters prepared in Embodiments 1-3 of the present application are bent 180° without complete blockage formation. In the figures, FIG. 1A is the control electrostatic spinning catheter, and FIG. 1B-FIG. 1D are the triple-layered catheters prepared in Embodiments 1-3 respectively.

Figure 2A:
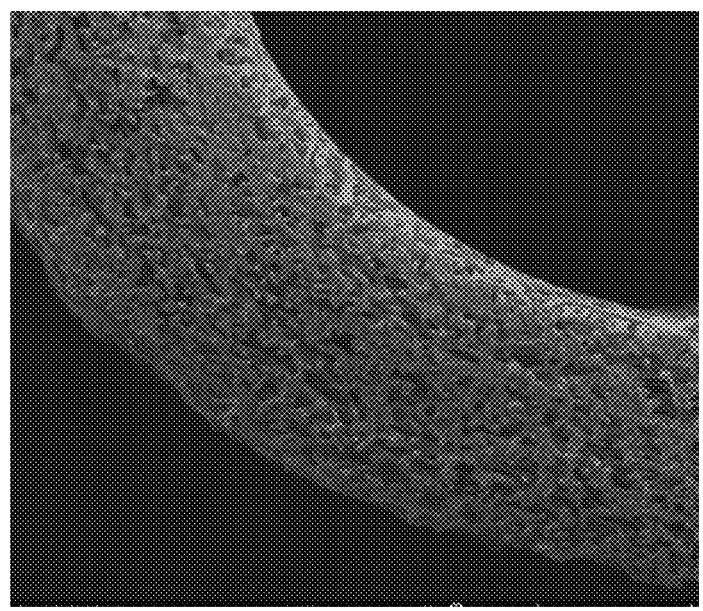
FIG. 2A shows the control electrostatic spinning catheter in terms of microstructure.
Figure 2B:
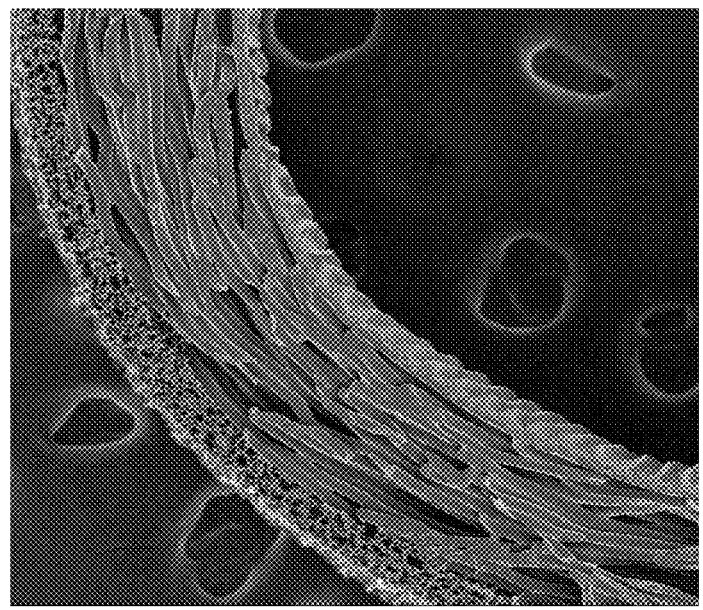
FIG. 2B shows the microstructure of the triple-layered catheters prepared in Embodiment 1
Figure 2C:
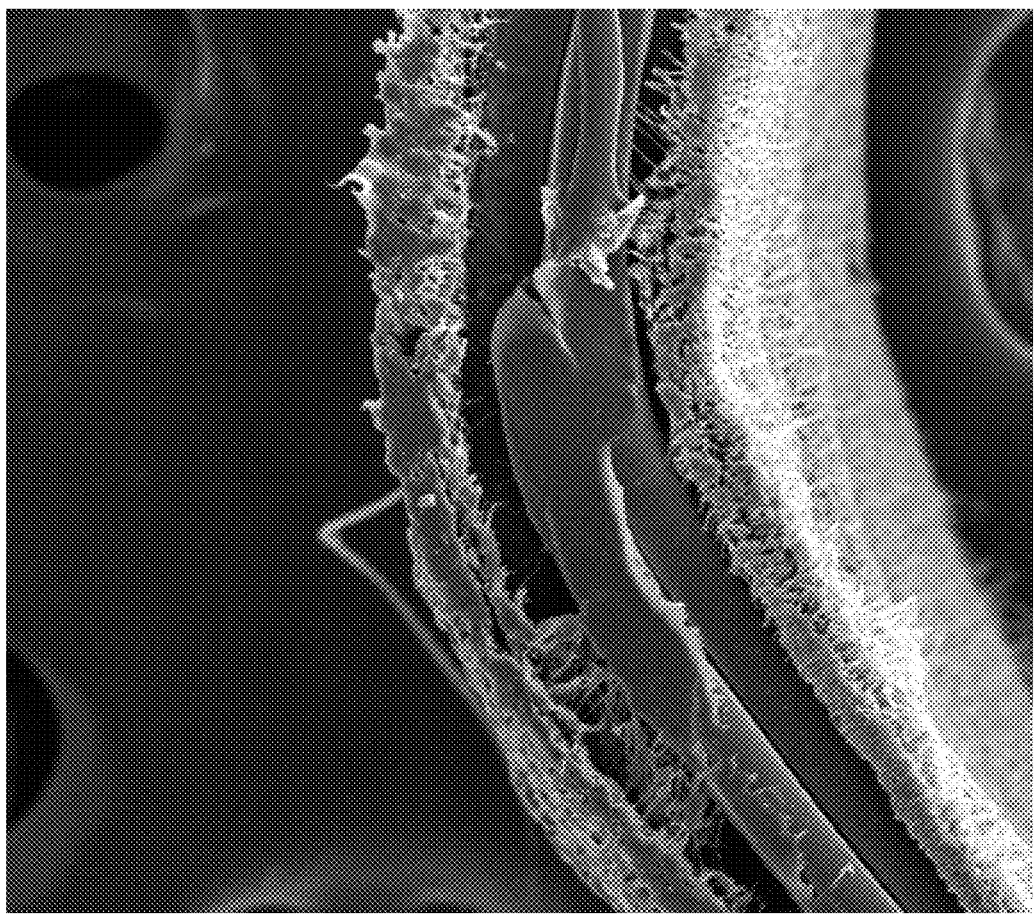
FIG. 2C shows the microstructure of the triple-layered catheters prepared in Embodiments 2.
Figure 2D:
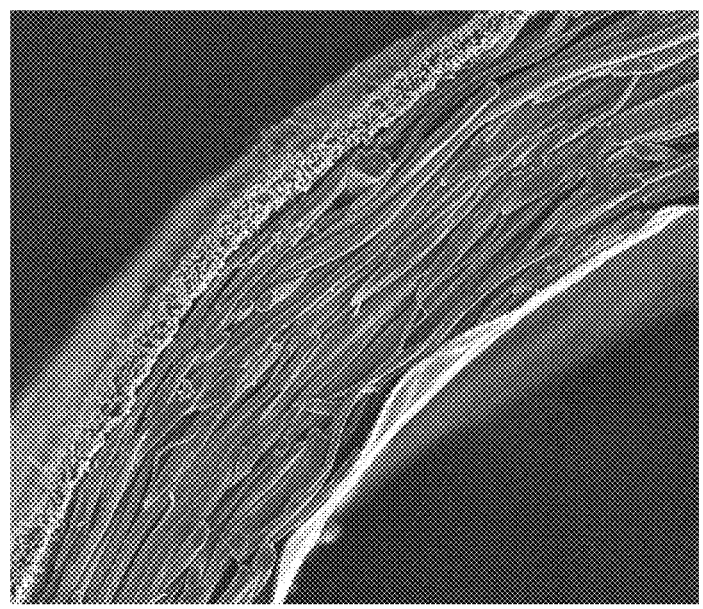
FIG. 2D shows the microstructure of the triple-layered catheters prepared in Embodiment 3.

The microstructures of the control electrostatic spinning catheter and the triple-layered catheters prepared in Embodiments 1-3 are shown in FIG. 2A-FIG. 2D, where FIG. 2A shows that of the control electrostatic spinning catheter and FIG. 2B-FIG. 2D show that of the triple-layered catheters prepared in Embodiments 1-3, respectively.

Figure 3A:
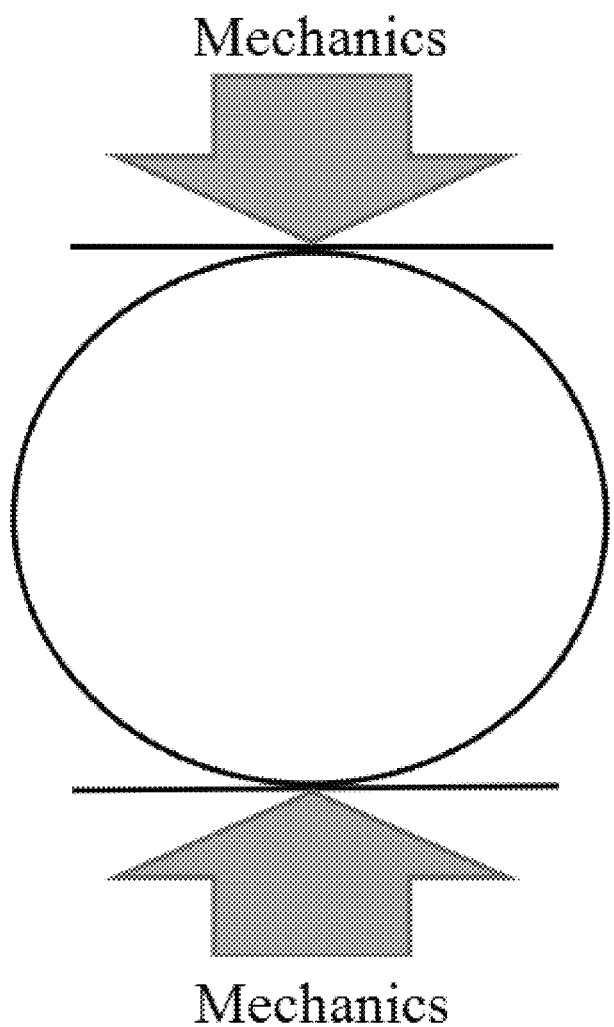
FIG. 3A shows a schematic diagram of the control electrostatic spinning catheter and the triple-layered catheters of Embodiments 1-3 for radial mechanical test.
Figure 3B:
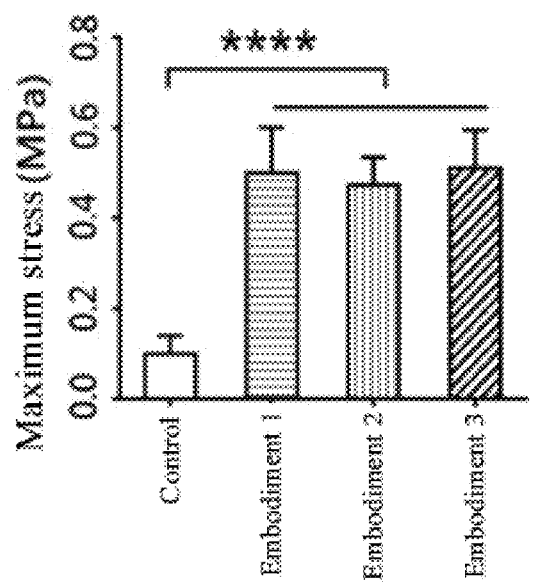
FIG. 3B shows results of the radial mechanical test.
Figure 4A:
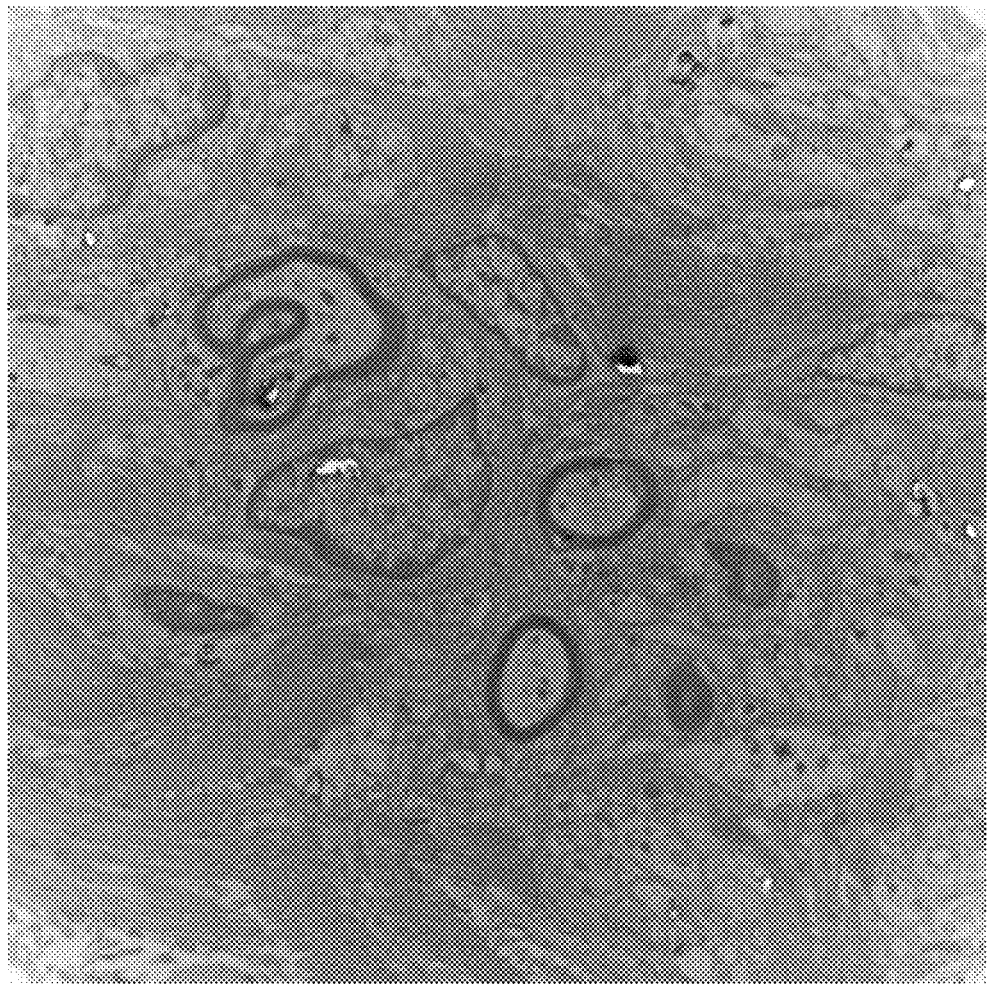
FIG. 4A shows morphology for regenerating myelin for peripheral nerve repair by transmission electron microscopy of the control electrostatic spinning catheter.
Figure 4B:
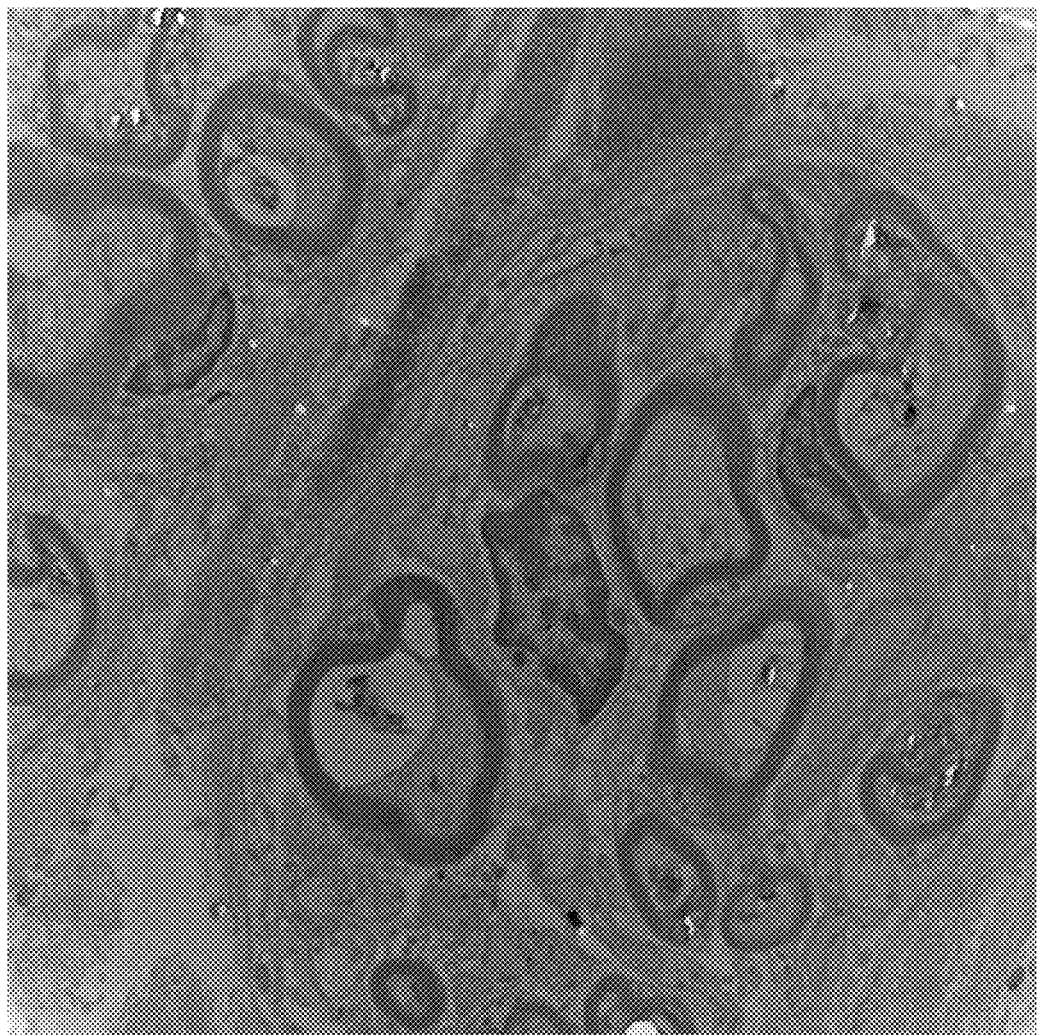
FIG. 4B, shows morphology for regenerating myelin for peripheral nerve repair by transmission electron microscopy of the triple-layered catheters prepared in Embodiment 1.
Figure 4C:
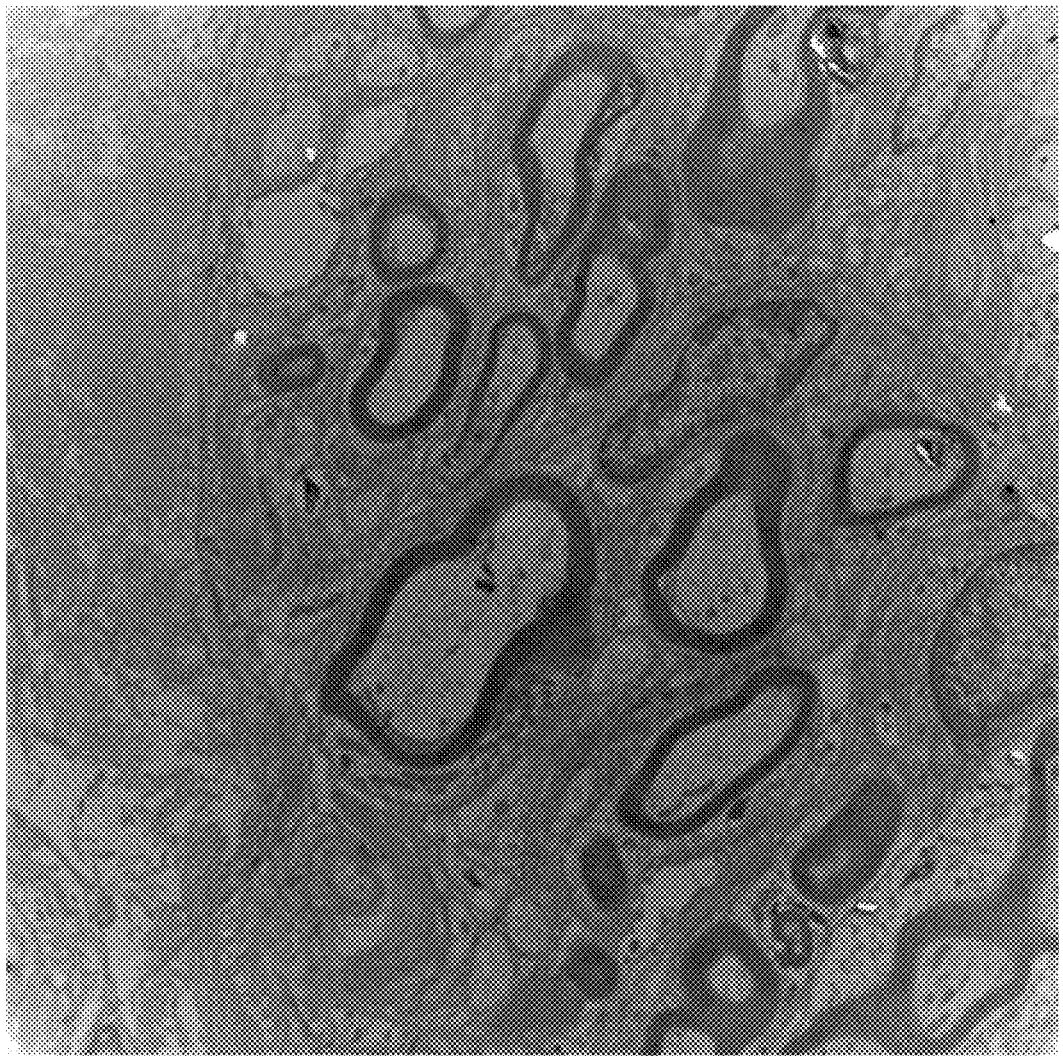
FIG. 4C shows morphology for regenerating myelin for peripheral nerve repair by transmission electron microscopy of the triple-layered catheters prepared in Embodiment 2.
Figure 4D:
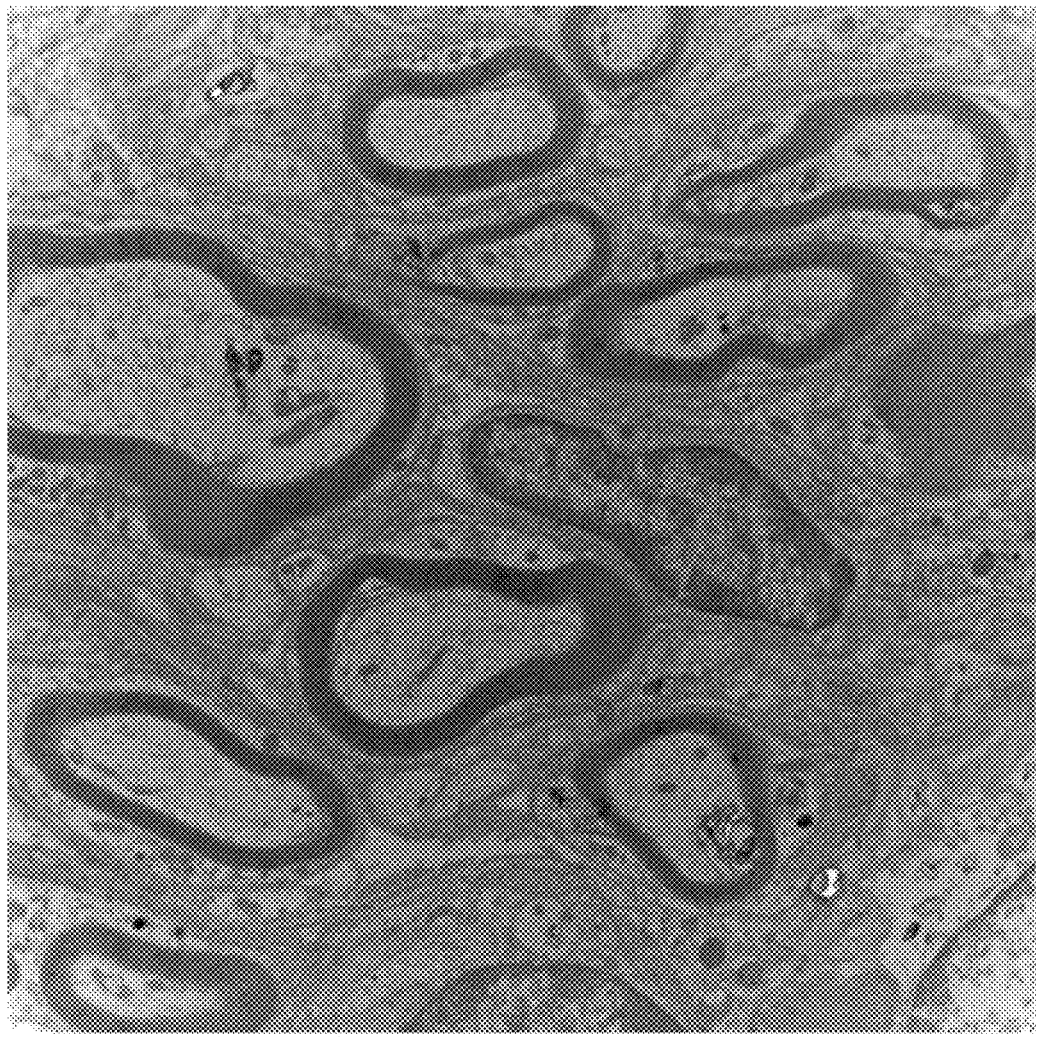
FIG. 4D shows morphology for regenerating myelin for peripheral nerve repair by transmission electron microscopy of the triple-layered catheters prepared in Embodiment 3.

Radial mechanical tests are conducted on the triple-layered catheters prepared in Embodiments 1-3, and the results are shown in FIG. 3A and FIG. 3B, where FIG. 3A is a schematic diagram of the radial mechanical tests, and FIG. B is the radial mechanical test results (**** in the figures indicates a significant difference with a P value<0.0001). The results of the radial mechanics test show that the radial mechanics of the catheter with the triple-layer structure of the present application is significantly higher than that of the control electrostatic spinning catheter.

The catheters of different structure are implanted into the defective parts of the sciatic nerve of rats for 3 months, after which the materials are taken for ultrathin section observation, and it is found that the thickness of the nerve regeneration myelin sheath guided by the catheter of the triple-layer structure of the present application is significantly higher than that of the control electrostatic spinning catheter (the results are shown in FIG. 4A-FIG. 4D).

Embodiment 4 Preparation of Triple-Layered Collagen (Col) Catheter

The collagen (Col) solutions used in this embodiment are all collagen acetic acid solutions (the content of collagen is expressed by mass/volume concentration).
  (1) preparation of the inner layer of the catheter: 1.0 g of collagen is weighed and dissolved in 50 mL of 0.5% acetic acid solution, and stirred overnight to obtain a collagen solution with a concentration of 2% (mass/volume), then the inner layer of the catheter is prepared by uniformly printing the solution as ink in a room temperature fume hood; specifically, a smooth stainless steel receiving rod with a diameter of 2.0 mm is installed on a printer, then the collagen solution is sucked into a syringe, which is then placed on an injection pump, with the syringe needle placed 0.5 mm above the stainless steel receiving rod; the advancing speed of the injection pump is set at 0.5 mL/h, the rotating speed of the receiving rod is 50 rpm, the lateral moving speed of the receiving rod is 0.3 mm/sec and the printing duration is 15 min; the prepared receiving rod has an inner layer of a thickness of 60 um, and the prepared receiving rod is vacuum dried at room temperature after the preparation;
  (2) preparation of the middle layer of the catheter: the middle layer of the catheter is prepared by wet spinning in a room temperature fume hood; specifically, the prepared receiving rod with the inner layer is installed on a wet spinning apparatus, 2% collagen spinning solution is sucked into a syringe, then the syringe is installed on an injection pump, and the needle of the syringe is placed at a position 1 cm away from the receiving rod in a spinning coagulation bath; the advancing speed of the injection pump is set to 1 mL/h, the receiving rod is set with a rotating speed of 400 rpm, a moving speed of 2 mm/sec, and the spinning duration is 50 min; coagulation bath and spinning solution solvent are removed after completion, and a middle layer with a fiber diameter of 40 um and a thickness of 370 um (fiber crossing angle of 20°) is produced;

(3) preparation of the outer layer of the catheter: the outer layer of the catheter is prepared by an electrostatic spinning method; specifically, the receiving rod with the inner layer and the middle layer prepared after the previous two steps is installed on an electrostatic spinning apparatus, 1% collagen solution is sucked into a syringe, then the syringe is installed on an injection pump, with the needle of the syringe placed at a position 20 cm above the receiving rod, and electrostatic spinning is carried out, where the voltage is set to 18 KV, the advancing speed of the injection pump is 1.5 mL/h, the receiving rod is set with a rotating speed of 1,000 rpm and a moving speed of 10 mm/sec, and the spinning duration is 50 min; after completion, the outer layer is vacuum dried at room temperature; the finished outer layer has a fiber diameter of 50 um and a thickness of 70 um, and it is then removed and set aside after the outer layer is spun (total thickness of 500 um, inner diameter of 2.0 mm).

Embodiment 5 Preparation of Triple-Layered Silk Fibroin Catheter

The silk fibroin solutions used in this embodiment are all silk fibroin aqueous solutions (the content of silk fibroin is expressed by mass/volume concentration).

(1) Preparation of the inner layer of the catheter: 2.0 g of degummed silk fibroin is weighed and dissolved in 10 mL of water solution, and stirred overnight to obtain a silk fibroin solution with a concentration of 20% (mass/volume); the inner layer of the catheter is prepared by uniformly printing using the solution as ink in a room temperature fume hood; specifically, a smooth stainless steel receiving rod with a diameter of 3.0 mm is installed on the printer; then the silk fibroin solution is sucked into a syringe, and the syringe is installed on the injection pump, with the syringe needle placed 0.3 mm above the stainless steel receiving rod; the advancing speed of the injection pump is set as 0.6 mL/h, the receiving rod is set with a rotating speed of 30 rpm, a lateral moving speed of 0.6 mm/sec, and the printing duration is set as 20 min; the obtained receiving rod has an inner layer with a thickness of 30 um and it is vacuum dried at room temperature after the preparation;

(2) preparation of the middle layer of the catheter: the middle layer of the catheter is prepared by wet spinning in a room temperature fume hood; specifically, a receiving rod with an inner layer is installed on a wet spinning apparatus, 20% silk fibroin spinning solution is sucked into a syringe, the syringe is installed on an injection pump, and the syringe needle is placed at a position 1.2 cm away from the receiving rod in a spinning coagulation bath; the advancing speed of the injection pump is set as 1.5 mL/h, the receiving rod is set with a rotating speed of 3050 rpm, a moving speed of 1 mm/sec, and the printing duration is set as 60 min; the coagulation bath and the spinning solution solvent are removed after completion, and the middle layer is produced with a fiber diameter of 120 um and a thickness of 390 um (fiber crossing angle of 90°);

(3) preparation of the outer layer of the catheter: the outer layer of the catheter is prepared by an electrostatic spinning method; specifically, the receiving rod with inner layer and middle layer prepared after the previous two steps is installed on an electrostatic spinning apparatus, 20% silk fibroin solution is sucked into a syringe, then the syringe is installed on an injection pump, with the needle of the syringe placed at a position 10 cm above the receiving rod, and electrostatic spinning is carried out, with the voltage set as 20 KV, the advancing speed of the injection pump set as 1.4 mL/h, the receiving rod is set with a rotating speed of 900 rpm and a moving speed of 112 mm/sec, and the spinning duration is set as 312 mm/sec; vacuum drying is carried out at room temperature after completion, and the prepared outer layer has a fiber diameter of 100 um and a thickness of 67 um; the triple-layered catheter (total thickness of 487 um, inner diameter of 3.0 mm) is removed and set aside after completion of the spinning of the outer layer.

Embodiment 6 Preparation of Triple-Layered Chitosan Catheter

The chitosan solutions used in this embodiment are all chitosan acetic acid solutions (the content of chitosan is expressed by mass/volume concentration).

(1) Preparation of the inner layer of the catheter: 0.3 g of chitosan powder is weighed and dissolved in 10 mL of 5% acetic acid solution (mass/volume), and stirred overnight to obtain a chitosan solution with a concentration of 3% (mass/volume); the inner layer of the catheter is then prepared by uniformly printing the solution as ink in a room temperature fume hood; specifically, a smooth stainless steel receiving rod with a diameter of 5.0 mm is installed on the printer, the chitosan solution is sucked into a syringe, and the syringe is installed on an injection pump, with the syringe needle placed at a position 0.1 mm above the stainless steel receiving rod; the advancing speed of the injection pump is set as 0.8 mL/h, the rotating speed of the receiving rod is set as 100 rpm, and the lateral moving speed is set as 1.6 mm/sec, the printing duration is set as 22 min; the receiving rod with an inner layer with a thickness of 100 um is vacuum dried at room temperature after preparation;

(2) preparation of the middle layer of the catheter: the middle layer of the catheter is prepared by wet spinning in a room temperature fume hood; specifically, a receiving rod with an inner layer is installed on a wet spinning apparatus, 3% chitosan spinning solution is sucked into a syringe, then the syringe is installed on an injection pump, with the needle of the syringe placed at a position 0.2 cm above the receiving rod in a spinning coagulation bath; the advancing speed of the injection pump is set as 0.5 mL/h, the rotating speed of the receiving rod is 2,000 rpm, the moving speed is 2 mm/sec, and the spinning duration is 27 min; the coagulation bath and spinning solution solvent are removed after completion, and the middle layer has a fiber diameter of 50 um and a thickness of 320 um (fiber crossing angle of 70°);

(3) preparation of the outer layer of the catheter: the outer layer of the catheter is prepared by an electrostatic spinning method; specifically, the receiving rod with inner layer and middle layer prepared after the previous two steps is installed on an electrostatic spinning apparatus, 3% chitosan solution is sucked into a syringe, and the syringe is installed on an injection pump, with the needle of the syringe placed at a position 12 cm above the receiving rod, and electrostatic spinning is carried out, with the voltage set as 20 KV, the advancing speed of the injection pump set as 1.7 mL/h, the rotating speed of the receiving rod is set as 600 rpm, the moving speed is set as 15 mm/sec, and the spinning duration is set as 25 min; vacuum drying at room temperature is carried out after completion; an outer layer of 1 um in diameter and 140 um in thickness is produced after the completion of the spinning of the outer layer, the triple-layered catheter (total thickness of 560 um and inner diameter of 5.0 mm) is removed and set aside for later use.

The above-mentioned embodiments only describe the preferred mode of the present application, and do not limit the scope of the present application. Under the premise of not departing from the design spirit of the present application, various modifications and improvements made by ordinary technicians in the field to the technical scheme of the present application shall fall within the protection scope determined by the claims of the present application.

What is claimed is:

1. A bending-resistant nerve catheter, comprising an inner layer, a middle layer and an outer layer, wherein the inner layer, the middle layer and the outer layer are made of raw materials of biodegradable polymers;
   the inner layer is a smooth surface inner layer, an oriented microchannel inner layer, or a fibrous inner layer capable of guiding directional migration of cells;
   the middle layer is a fibrous middle layer with crossing angles, which is used to provide radial mechanical support; and
   the outer layer is a fibrous outer layer distributed randomly;
   the smooth surface inner layer has a thickness of 1-100 micrometers, the oriented microchannel inner layer has a thickness of 1-200 micrometers, or the fibrous inner layer has a fiber diameter of 0.1-200 micrometers and a thickness of 0.1-200 micrometers;
   the fibrous middle layer of crossing angles is prepared by wet spinning or melt spinning;
   the fibrous outer layer comprises fibers of a diameter of 0.01-200 micrometers, and the outer layer has a thickness of 10-400 micrometers; and
   the bending-resistant nerve catheter forms no complete blockage after 180° bending.

2. The bending-resistant nerve catheter according to claim 1, wherein the bending-resistant nerve catheter has a lumen diameter of 1-100 millimeters and a wall thickness of 50-1,000 micrometers.

3. The bending-resistant nerve catheter according to claim 1, wherein the wet spinning prepares fibers with a diameter of 5-300 micrometers, and the middle layer has a thickness of 20-450 micrometers; or the melt spinning prepares fibers with a diameter of 1-100 micrometers, and the middle layer has a thickness of 20-500 micrometers.

4. The bending-resistant nerve catheter according to claim 1, wherein the biodegradable polymers comprise one or more of synthetic degradable polymers or natural polymer materials.

5. The bending-resistant nerve catheter according to claim 4, wherein the synthetic degradable polymers comprise polylactic acid, polycaprolactone, poly(L-lactide-caprolactone), polyhydroxyalkanoates, poly(lactic-co-glycolic acid), polydioxanone or polyurethane; and the natural polymer materials comprise collagen, gelatin, silk fibroin, fibrin, chitosan, chitin, cellulose, starch, alginic acid or hyaluronic acid.

* * * * *